United States Patent [19]

Buchecker et al.

[11] Patent Number: 5,399,689

[45] Date of Patent: Mar. 21, 1995

[54] CHLOROPHENYLALKOXYALKYL COMPOUNDS

[75] Inventors: Richard Buchecker, Zurich; Martin Schadt, Seltisberg, both of Switzerland; Haruyoshi Takatsu, Tokyo, Japan

[73] Assignee: Hoffmann-La Roche Inc., Nutley, N.J.

[21] Appl. No.: 17,353

[22] Filed: Feb. 11, 1993

Related U.S. Application Data

[63] Continuation of Ser. No. 751,901, Aug. 29, 1991, abandoned.

[30] Foreign Application Priority Data

Sep. 10, 1990 [CH] Switzerland .................. 2931

[51] Int. Cl.$^6$ .................. C07C 43/168; C07D 403/06; C07D 241/12
[52] U.S. Cl. .................. 544/296; 544/333; 544/335; 544/357; 544/405; 546/255; 546/256; 546/268; 546/344; 568/661
[58] Field of Search .................. 568/661; 544/296, 333, 544/335, 357, 405; 546/255, 256, 268, 344, 346; 549/370, 374

[56] References Cited

U.S. PATENT DOCUMENTS

| | | | |
|---|---|---|---|
| 4,710,315 | 12/1987 | Schad et al. | 568/661 |
| 4,846,998 | 7/1989 | Pohl et al. | 568/559 |
| 4,871,470 | 10/1989 | Wächtler et al. | 568/661 |
| 4,943,384 | 7/1990 | Sucrow et al. | 252/299.61 |
| 5,068,462 | 11/1991 | Sasaki et al. | 568/659 |

FOREIGN PATENT DOCUMENTS

| | | |
|---|---|---|
| 58981 | 9/1986 | European Pat. Off. . |
| 354434 | 2/1990 | European Pat. Off. . |
| 415 090 | 7/1990 | European Pat. Off. . |
| 1225147 | 10/1986 | Japan .................. 568/661 |
| 90/15114 | 12/1990 | WIPO . |

OTHER PUBLICATIONS

Derwent Abstract 91-059121/09 of DE 4,025,818.
Derwent Abstract 91-074773/11 of DE 4,027,840.

*Primary Examiner*—Johann Richter
*Assistant Examiner*—John Peabody
*Attorney, Agent, or Firm*—George M. Gould; George W. Johnston

[57] ABSTRACT

The present invention is concerned with novel chlorophenylalkoxyalkyl compounds of the general formula

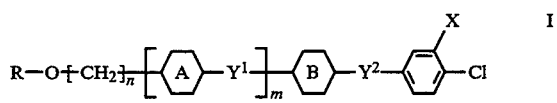

wherein R denotes an alkyl residue with 1 to 12 carbon atoms; n is a whole number of 2 to 7, ring A denotes trans-1,4-cyclohexylene or 1,4-phenylene; m is either 0 or 1; ring B is trans-1,4-cyclohexylene, 1,4-phenylene in which optionally one CH group or two non-adjacent CH groups is/are replaced by nitrogen or, when m stands for 1, also trans-1,3-dioxane-2,5-diyl; $Y^1$ and $Y^2$ each independently represent a single covalent bond or —$CH_2CH_2$—; and X denotes hydrogen, fluorine or chlorine, their manufacture, liquid crystalline mixtures which contain these compounds, their production and use for electro-optical purposes.

18 Claims, No Drawings

CHLOROPHENYLALKOXYALKYL COMPOUNDS

This is a continuation of U.S. application Ser. No. 07/751,901, filed Aug. 29, 1991, now abandoned.

BACKGROUND

1. Field of the Invention

The present invention is concerned with novel chlorophenylalkoxyalkyl compounds, their manufacture, liquid crystalline mixtures which contain these compounds and their use for electro-optical purposes.

2. Description

Liquid crystals are used primarily as dielectrics in indicating devices, since the optical properties of these substances can be influenced by an applied voltage. Electro-optical devices based on liquid crystals are well-known to a person skilled in the art and can be based on various effects. Examples of such devices are cells having dynamic scattering, DAP cells (deformation of aligned phases), guest/host cells, TN cells having a twisted nematic structure, STN cells ("super-twisted nematic"), SBE cells ("super-birefringence effect") and OMI cells ("optical mode interference") and recently, having regard to the interest in actively addressed liquid crystal applications, also TFT cells (thin film transistor). The most common indicating devices are based on the Schadt-Helfrich effect and have a twisted nematic structure.

The liquid crystal materials must have a good chemical and thermal stability and a high stability towards electric fields and electro-magnetic radiation. They should have a low viscosity and in the cells should give short response times, low threshold potentials and a high contrast. Furthermore, at usual operating temperatures they should should have a suitable mesophase, for example a nematic, cholesteric or chiral tilted smectic phase. Further properties such as the electrical conductivity, the dielectric anisotropy and the optical anisotropy must fulfil different requirements depending on the type of cell and field of application. For example, materials for cells having a twisted nematic structure should have a positive dielectric anisotropy and an electrical conductivity which is as low as possible. In addition to the general interest in liquid crystal materials having a high optical anisotropy there has recently been an increased in materials having a low optical anisotropy, especially for actively addressed liquid crystal indicators, e.g. in the case of TFT applications (thin film transistor) in television sets.

In order to optimize the properties liquid crystals are usually used as mixtures of several components. It is therefore important that the components have a good miscibility with one another.

SUMMARY OF THE INVENTION

The present invention provides compounds of the formula

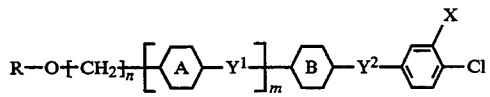

wherein R denotes an alkyl residue with 1 to 12 carbon atoms; n is a whole number of 2 to 7, ring A denotes trans-1,4-cyclohexylene or 1,4-phenylene; m is either 0 or 1; ring B is trans-1,4-cyclohexylene, 1,4-phenylene in which optionally one CH group or two non-adjacent CH groups is/are replaced by nitrogen or, when m stands for 1, also trans-1,3-dioxane-2,5-diyl; $Y^1$ and $Y^2$ each independently represent a single covalent bond or —$CH_2CH_2$—; and X denotes hydrogen, fluorine or chlorine.

The compounds in accordance with the invention are liquid crystals having comparatively high clearing points and a broad nematic phase. It has surprisingly been found that in spite of the voluminous chlorine end group the compounds of formula I have comparatively short switching times, especially in indicating devices having a nematic structure.

By virtue of their high specific resistances, their low ion solubility and the above-mentioned comparatively short switching times the compounds of formula I in accordance with the invention are especially suitable for TFT applications.

DETAILED DESCRIPTION OF THE INVENTION

The present invention pertains to compounds of the formula:

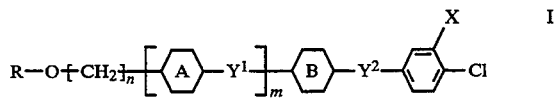

wherein R is alkyl of 1 to 12 carbon atoms; n is an integer from 2 to 7; ring A is trans-1,4-cyclohexylene or 1,4-phenylene; m is either 0 or 1; ring B is trans-1,4-cyclohexylene, 1,4-phenylene, pyridin-2,5-diyl, pyrimidin-2,5-diyl or pyrazin-2,5-diyl; or when m is 1, ring B also can be trans-1,3-dioxane-2,5-diyl; $Y^1$ and $Y^2$ each independently are a single covalent bond or —$CH_2CH_2$—; and X is hydrogen, fluorine or chlorine.

As used herein, the term "alkyl" embraces a straight-chain or branched alkyl group with 1 to 12 carbon atoms.

The term "1,4-phenylene in which optionally one CH group or two non-adjacent CH groups are replaced by nitrogen" includes 1,4-phenylene, pyridine-2,5-diyl, pyrimidine-2,5-diyl or pyrazine-2,5-diyl.

Compounds of formula I in which ring A is 1,4-cyclohexylene are particularly preferred. Ring B preferably is 1,4-cyclohexylene or 1,4-phenylone.

Preferably, R is a straight-chain alkyl residue with 1 to 5 carbon atoms, and in particular, a straight-chain alkyl residue with 1 to 3 carbon atoms.

Preferred compounds of formula I are compounds in which n is from 2 to 5. Further, compounds in which at least one of the group $Y^1$ and $Y^2$ is a single covalent bond are preferred.

The compounds of the following formulas are preferred aspects of compounds of formula I

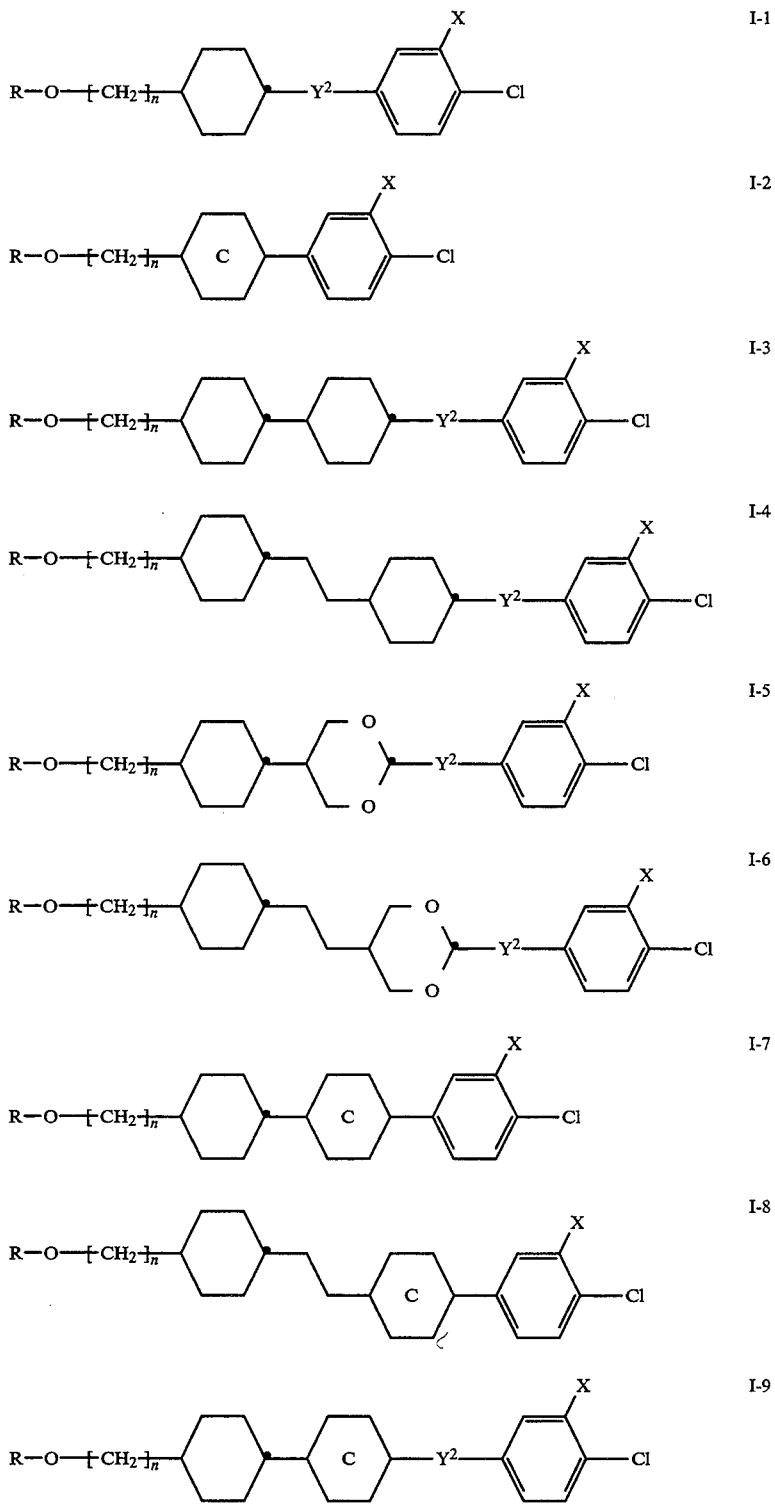

wherein R, $Y^2$ and X have the significance given above for formula I; and ring C is 1,4-phenylene, pyridine-2,5-diyl or pyrimidine-2,5-diyl.

Ring C in formulae I-2, I-7 and I-8 preferably is 1,4-phenylene.

The preparation of the compounds of formula I can be effected in a manner known per se. Preferred methods are illustrated on the basis of the following Schemes in which R and B have the definitions given above for formula I and n stands for an integer from 1 to 3.

Scheme 1
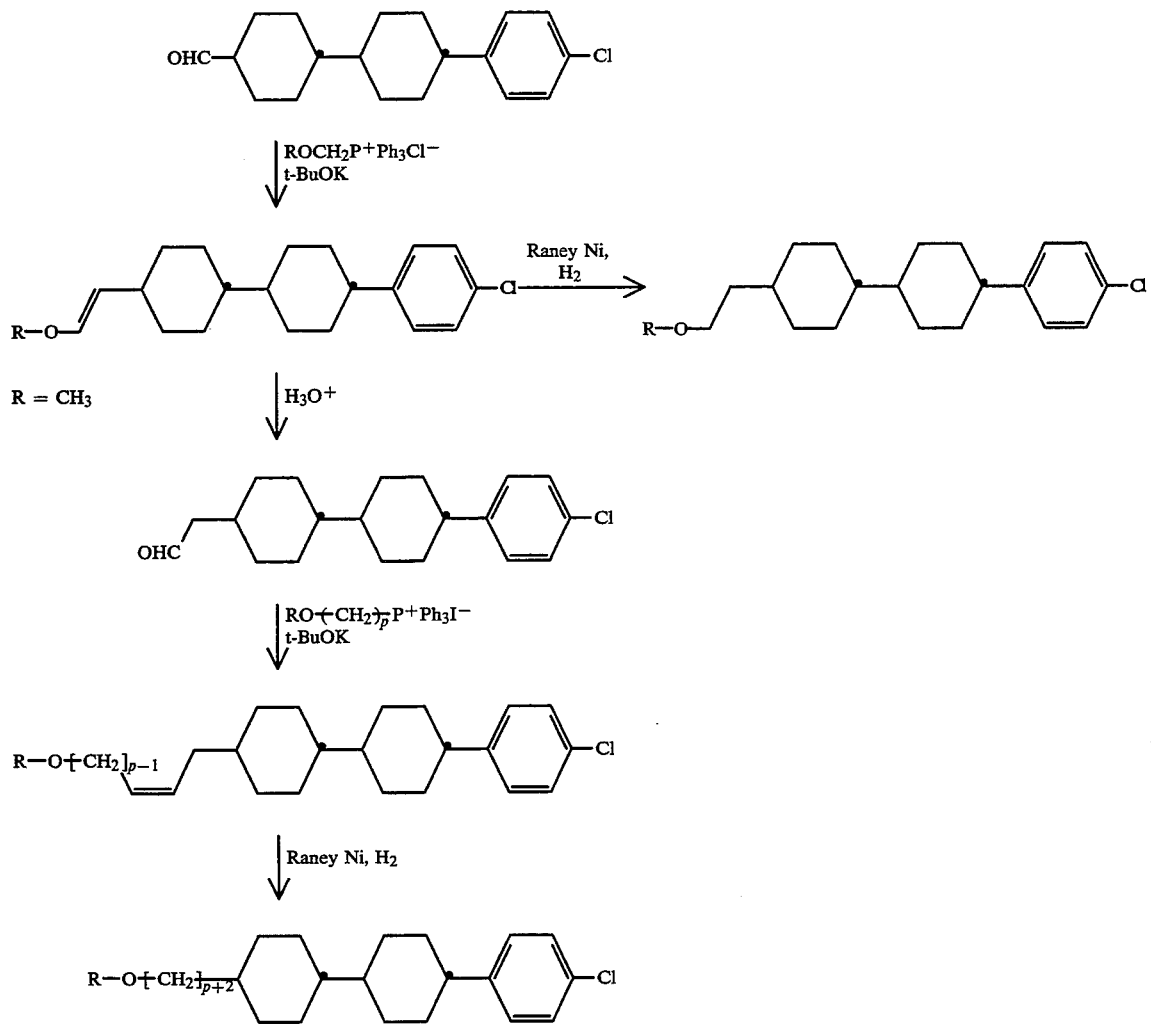
Scheme 2
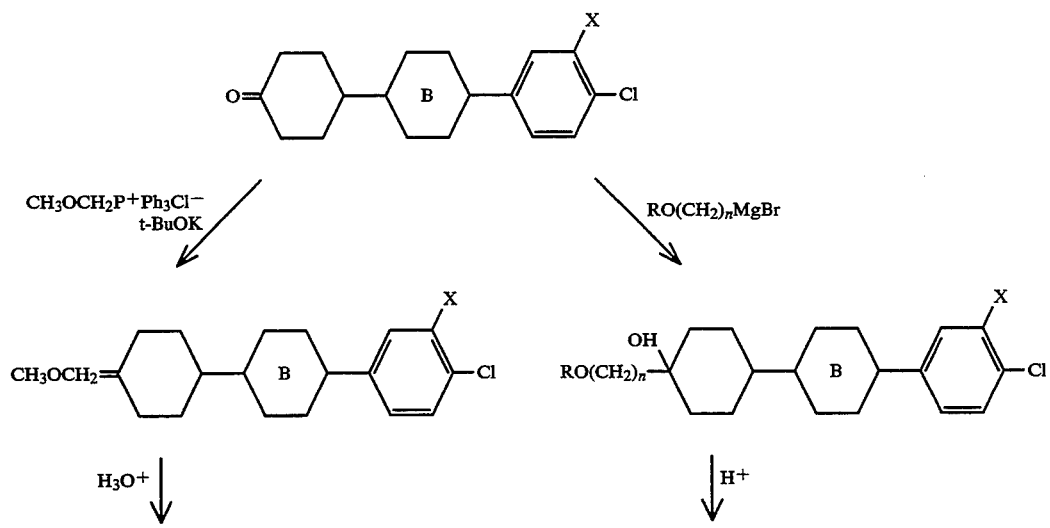

5,399,689
Scheme 2
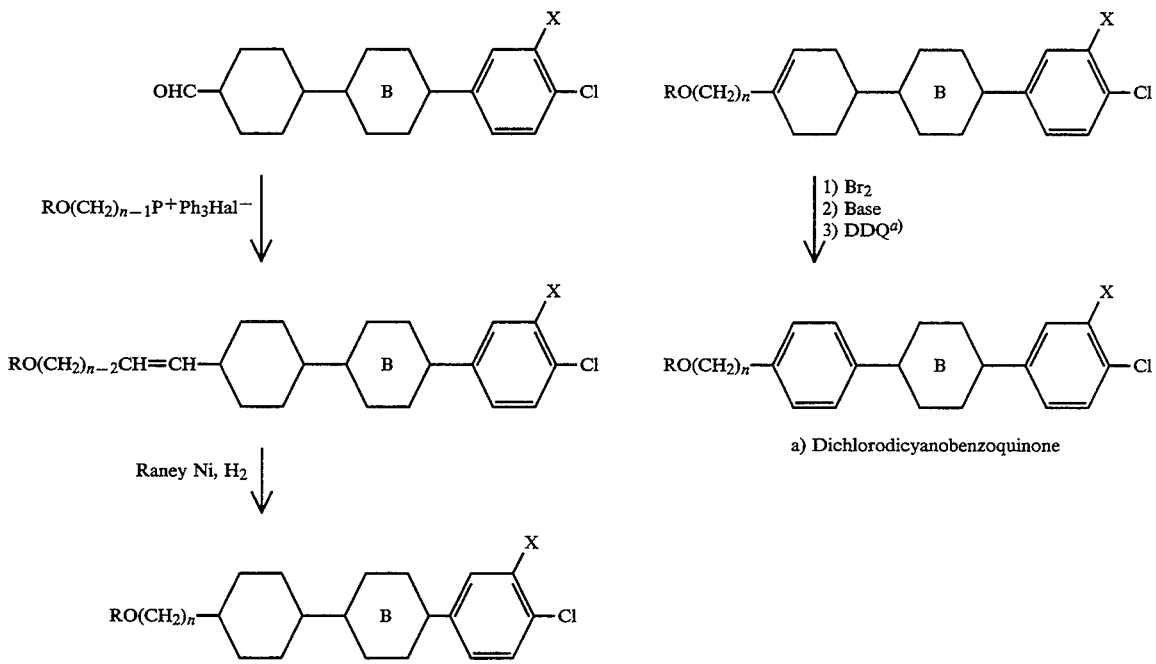
a) Dichlorodicyanobenzoquinone
Scheme 3
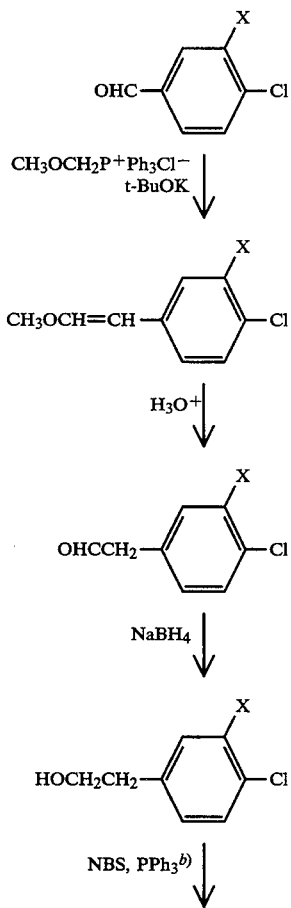

-continued
Scheme 3
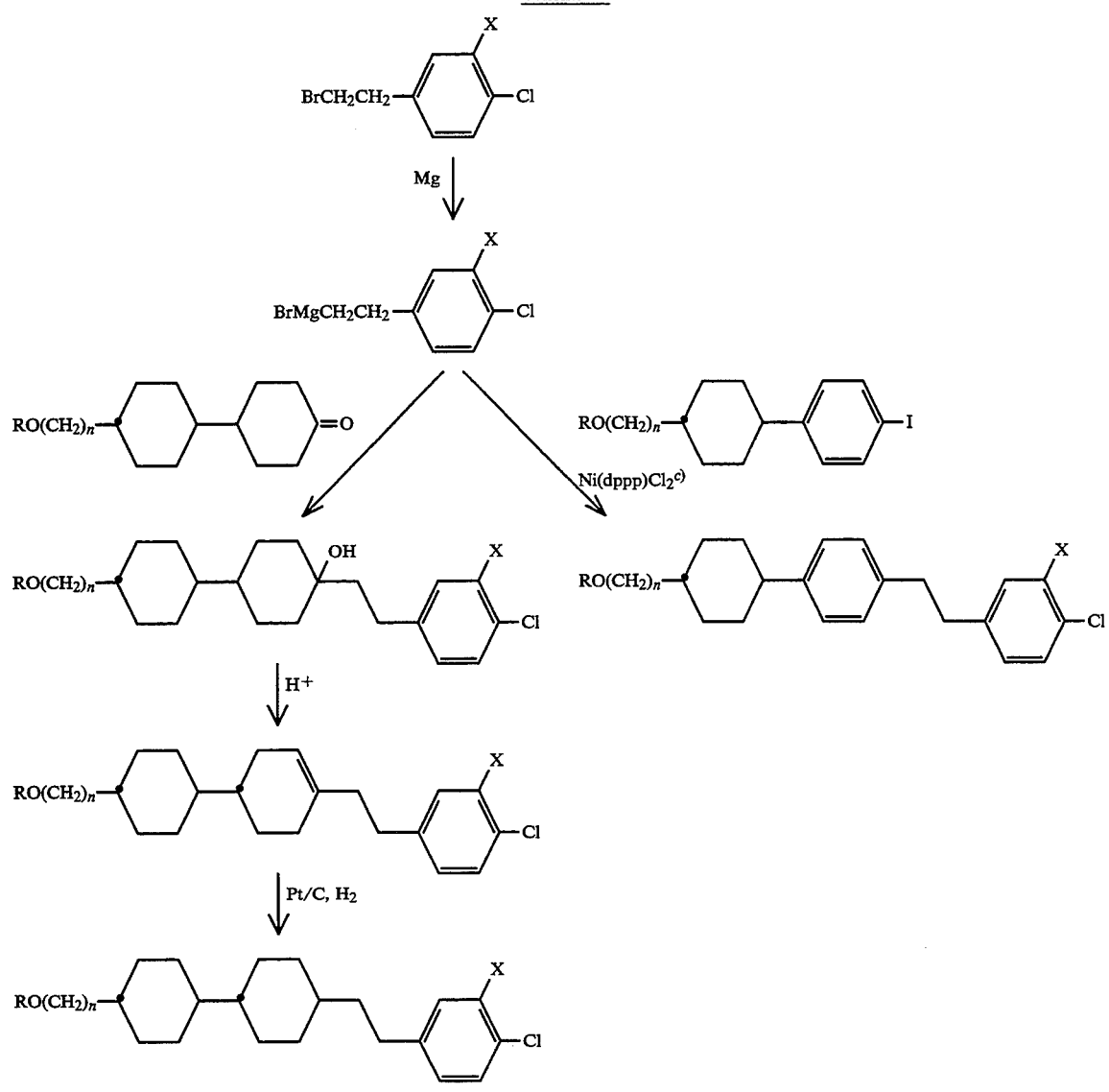
b) N-Bromosuccinimide
c) Bis(1,3-diphenylphosphino)-propane nickel(II) chloride
Scheme 4
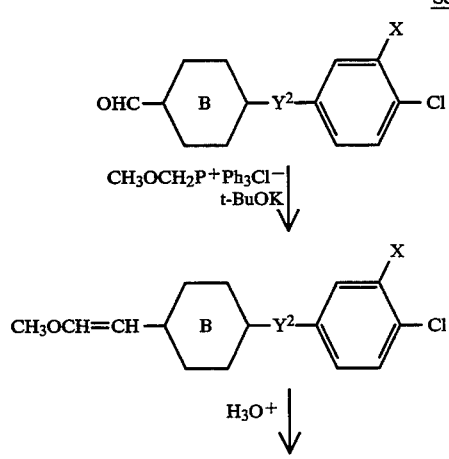

-continued
Scheme 4
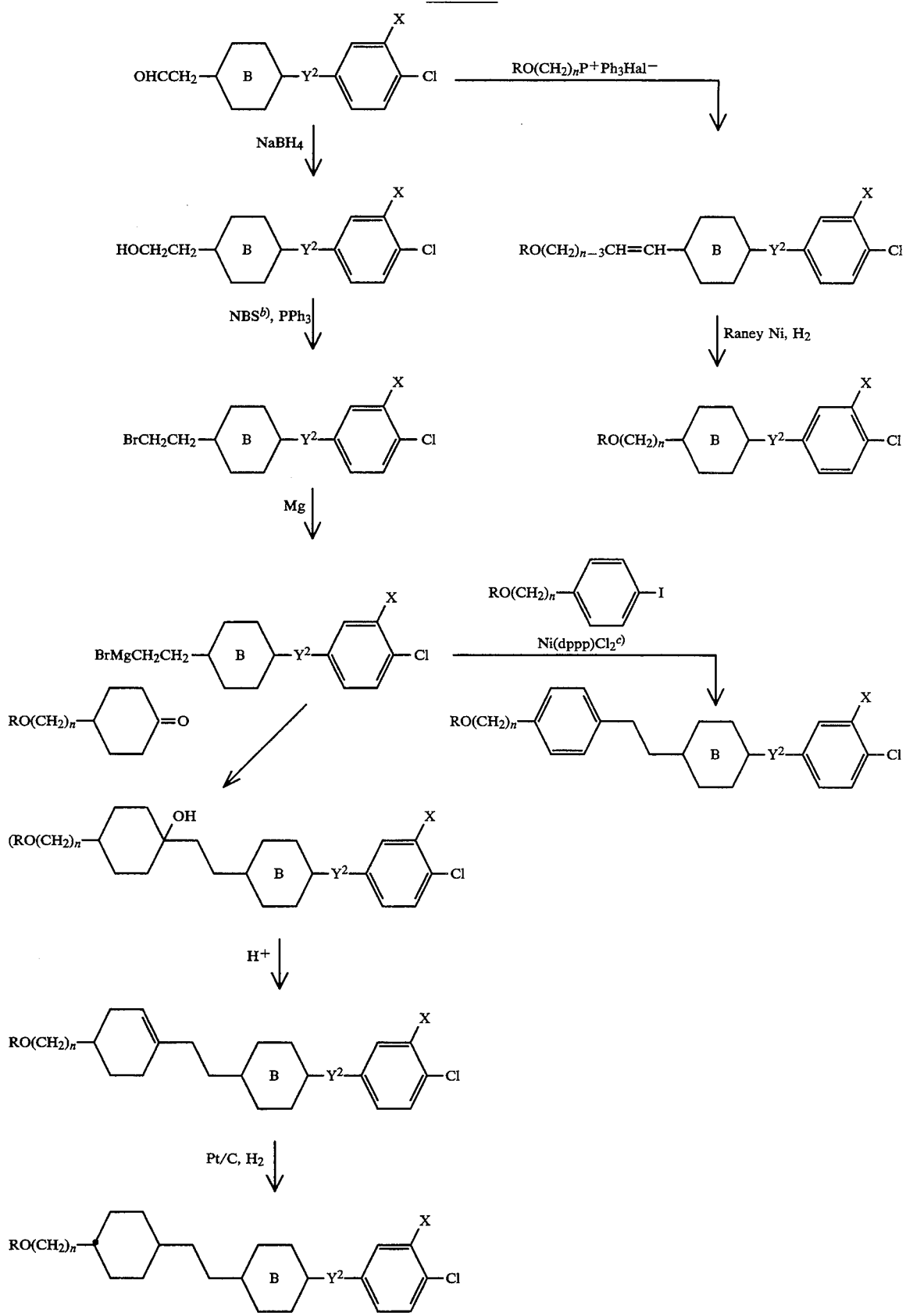

In the above formulae, R, X, n, ring B, and $Y^2$ have the definitions given above in formula I, and p is an integer from 1 to 5.

The starting materials are known or are analogues of known compounds and can be prepared according to known methods.

The compounds of formula I in accordance with the invention have good miscibility with one another and/or with other liquid crystal components. In liquid crystalline mixtures they lead to a broad nematic mesophase, low threshold potentials and short response times.

The liquid crystalline mixtures in accordance with the invention contain at least two components, of which at least one component is a compound of formula I. A second component, and optionally additional components, can be other compounds of formula I or other liquid crystal components. Because of the good solubility of the compounds of formula I and because of their good miscibility with one another, they can be present in the mixtures in accordance with the invention in relatively high amounts. In general, however, an amount of about 1–50 wt. %, especially about 5–30 wt. %, of compounds of formula I is preferred.

The mixtures in accordance with the invention preferably contain, in addition to one or more compounds of formula I, one or more compounds from the group of compounds of the formulae

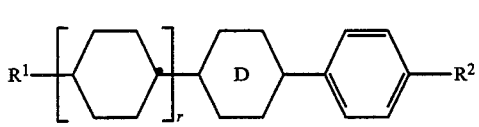

II

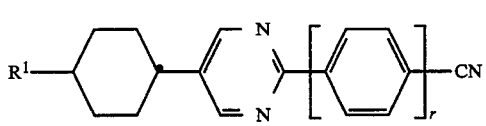

III

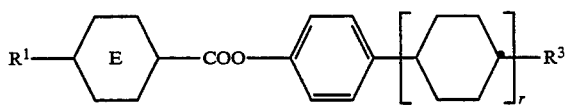

IV

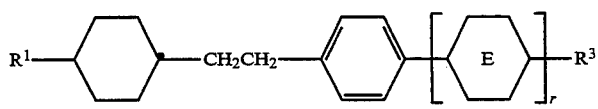

V

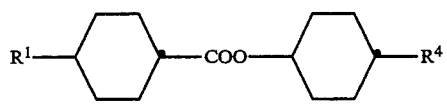

VI

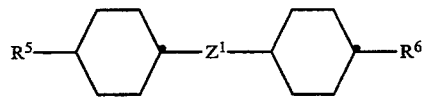

VII

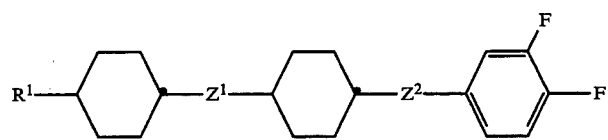

VIII

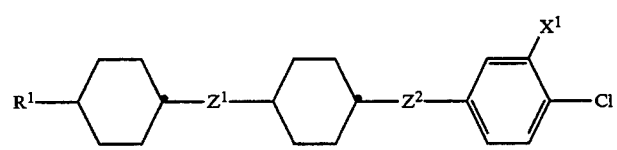

IX

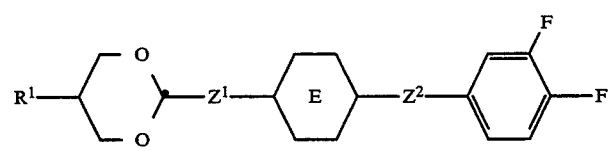

X

-continued

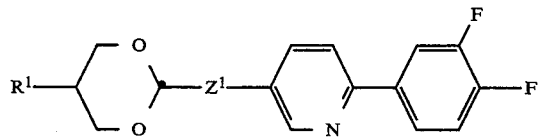 XI

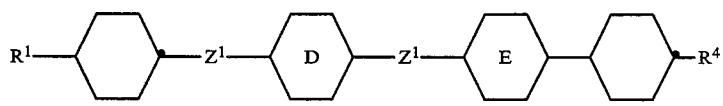 XII

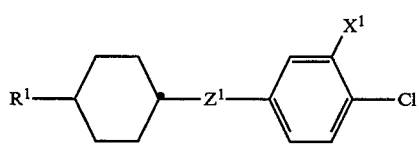 XIII

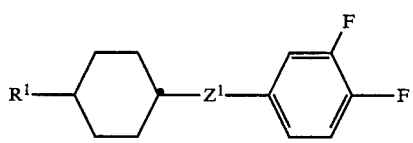 XIV

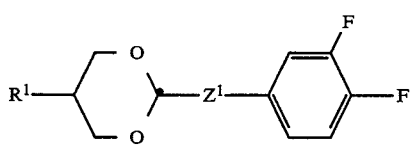 XV

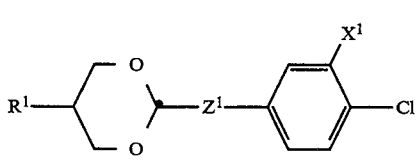 XVI

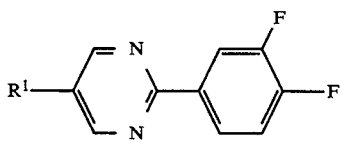 XVII

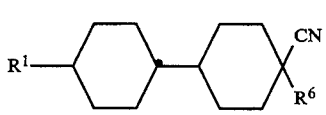 XVIII

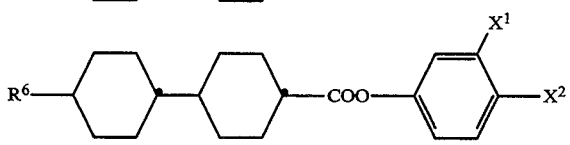 XIX

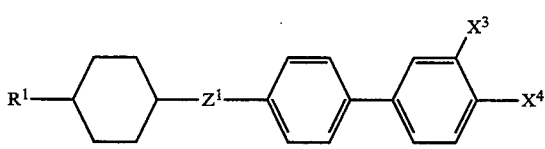 XX wherein r is either 0 or 1; $R^1$ and $R^4$ each independently are alkyl, alkoxyalkyl, 3E-alkenyl, 4-alkenyl or when bonded to trans-1,4-cyclohexylene or trans-1,4-dioxan-2,5-diyl, $R^1$ and $R^4$ also can be each independently 1E-alkenyl; ring D is 1,4-phenylene, trans-1,4-cyclohexylene, pyridine-2,5-diyl, pyrimidine-2,5-diyl or trans-1,3-dioxane-2,5-diyl; $R^2$ is cyano, —NCS, fluorine, alkyl, 3E-alkenyl, 4-alkenyl, alkoxy, 2E-alkenyloxy, 3-alkenyloxy of 1-alkynyl; ring E is 1,4-phenylene or trans-1,4-cyclohexylene; $R^3$ is alkyl, 3E-alkenyl, 4-alkenyl or when bonded to a trans-1,4-cyclohexylene ring, $R^3$ also can be 1E-alkenyl, or when bonded to a 1,4-phenylene ring, $R^3$ also can be cyano, —NCS, alkoxy, 2E-alkenyloxy or 3-alkenyloxy; $R^5$ is alkyl, 1E-alkenyl, 3E-alkenyl or 4-alkenyl; $Z^1$ and $Z^2$ each independently are a single covalent bond or —CH$_2$CH$_2$—, provided that when bonded between two aromatic rings, $Z^1$ and $Z^2$ are always a single covalent bond; $R^6$ is cyano, alkyl, 1E-alkenyl, 3E-alkenyl, 4-alkenyl, alkoxy, 2E- alkenyloxy, 3-alkenyloxy, alkoxymethyl or (2E-alkenyl-)oxy-methyl; $X^1$ is hydrogen, chlorine or fluorine; $X^2$ is cyano, chlorine or fluorine; $X^3$ is hydrogen or fluorine; and $X^4$ is chlorine or fluorine.

The term "aromatic rings" as used herein, includes, without limitation, substituted and unsubstituted 1,4-phenylene, pyridine-2,5-diyl, pyrimidine-2,5-diyl and pyrazine-2,5-diyl.

By the term "alkoxy" what is meant is the group —OJ—, wherein J is alkyl as defined hereinabove.

As used herein, the term "alkenyl" means a straight-chain or branched alkyl group having at least one double bond. For example, vinyl, 1E-propenyl, 1E-butenyl, 3E-butenyl, 1E-pentenyl, 3E-pentenyl, E-hexenyl, 3E-hexenyl, 4-pentenyl, etc.

By the term "alkenyloxy", what is meant is the group —O—Q wherein Q is an alkenyl as defined hereinabove.

As used herein, the term "alkoxyalkyl" means the group —J—O—J wherein J is an alkyl as defined hereinabove.

By the term "alkenyloxyalkyl" what is meant is the group —J—O—Q wherein J is an alkyl and Q is an alkenyl as defined above.

As used herein "1-alkynyl" means an alkyl group as defined above and having a triple-bond in position 1.

Residues $R^1$ to $R^6$ each preferably have a maximum of 12 carbon atoms, especially a maximum of 7 carbon atoms. Straight-chain residues are generally preferred.

The preparation of the liquid crystalline mixtures and of the electro-optical devices can be effected in a manner known per se.

The invention is illustrated in more detail by the following Examples. In the Examples, C signifies a crystalline phase, N signifies a nematic phase and I signifies the isotropic phase. $V_{10}$ denotes the voltage for 10% transmission. $T_{on}$ and $T_{off}$ denote, respectively, the switching-on time and the switching-off time. An denotes the optical anisotropy. Unless otherwise stated, the following examples were carried out as stated.

Example 1

5.4 g of 1-chloro-4-[trans-4-(5-methoxy-2-pentenyl)-cyclohexyl]benzene are dissolved in 80 ml of ethyl acetate in an autoclave, treated with 1 g of Raney nickel and hydrogenated for 7 hours at 60° C. and 5 kg/cm². The suspension is filtered and evaporated. The residue (5.2 g) is crystallized twice from 30 ml of ethanol each time and gives 3.4 g of 1-chloro-4-[trans-4-(5-methoxypentyl)cyclohexyl]benzene; m.p. (C—I) 52.8° C.

The 1-chloro-4-[trans-4-(5-methoxy-2-pentenyl)cyclohexyl]benzene used as the starting material is prepared as follows:

a) A suspension, gassed with nitrogen, of 9.3 g of (methoxymethyl)triphenylphosphonium chloride in 40 ml of tetrahydro-furan is cooled to −5° C. and treated with 3.9 g of potassium tert.-butylate. The suspension is stirred at −5° C. for 10 minutes and at room temperature for 1 hour, again cooled to −5° C. and treated within 5 minutes with a solution of 5 g of trans-4-(4-chloro-phenyl)cyclohexanecarboxaldehyde in 20 ml of tetrahydrofuran. After stirring at −5° C. for 10 minutes and at room temperature for 1 hour 50 ml of water are added thereto and the aqueous phase is extracted with 100 ml of ethyl acetate. The organic phase is washed with water, dried over sodium sulphate, filtered and evaporated. The residue is stirred with 100 ml of hexane for 1 hour, filtered off and washed with 50 ml of hexane. The filtrate is concentrated and gives 5 g of 1-chloro-4-[trans-4-(2-methoxyvinyl))cyclohexyl]benzene.

b) 5 g of 1-chloro-4-[trans-4-(2-methoxyvinyl)cyclohexyl]-benzene in 60 ml of tetrahydrofuran and 20 ml of 9 percent hydrochloric acid are stirred at 60° C. for 2 hours. After cooling to room temperature the aqueous phase is extracted with 100 ml of ethyl acetate. The organic phase is washed with water, dried over sodium sulphate, filtered and evaporated. The residue gave 4.6 g of [trans-4-(4-chlorophenyl)cyclohexyl]acetaldehyde.

c) A suspension, gassed with nitrogen, of 11.4 g of (3-methoxypropyl)triphenylphosphonium iodide in 50 ml of tetra- hydrofuran is cooled to −5° C., treated with 3.36 g of potassium tert.-butylate, stirred at −5° C. for 10 minutes and at room temperature for 1 hour. After cooling the reaction mixture to −5° C. a solution of 4.6 g of [trans-4-(4-chlorophenyl)cyclo-hexyl]acetaldehyde in 25 ml of tetrahydrofuran is added dropwise within 5 minutes, the mixture is stirred at −5° C. for 10 minutes and at room temperature for 1 hour, treated with 50 ml of water and the aqueous phase is extracted with 100 ml of ethyl acetate. The organic phase is washed with water, dried over sodium sulphate, filtered and concentrated. The residue is taken up in 50 ml of toluene and dissolved by heating to 70° C. and stirring for 30 minutes. The solution is cooled to room temperature, treated with 50 ml of hexane, stirred for 2 hours, filtered and washed with 30 ml of toluene/hexane (1:1 vol.). The filtrate is filtered over 100 g of silica gel and the silica gel is washed with 200 ml of hexane/toluene (1:1 vol.). The filtrate; is concentrated and gives 5.4 g of 1-chloro-4-[trans-4-(5-methoxy-2-pentenyl)cyclohexyl]benzene. The following compounds can be manufactured in an analogous manner:

1-Chloro-4-[trans-4-(3-methoxypropyl)cyclohexyl]benzene,
1-chloro-4-[trans-4-(3-ethoxypropyl)cyclohexyl]benzene,
1-chloro-4-[trans-4-(3-propoxypropyl)cyclohexyl]benzene,
1-chloro-4-[trans-4-(4-methoxybutyl)cyclohexyl]benzene,
1-chloro-4-[trans-4-(4-ethoxybutyl)cyclohexyl]benzene,
1-chloro-4-[trans-4-(5-ethoxypentyl)cyclohexyl]benzene,
1,2-dichloro-4-[trans-4-(3-methoxypropyl)cyclohexyl]-benzene,
1,2-dichloro-4-[trans-4-(3-ethoxypropyl)cyclohexyl]-benzene,
1,2-dichloro-4-[trans-4-(3-propoxypropyl)cyclohexyl]-benzene,
1,2-dichloro-4-[trans-4-(4-methoxybutyl)cyclohexyl]-benzene,
1,2-dichloro-4-[trans-4-(4-ethoxybutyl)cyclohexyl]-benzene,
1,2-dichloro-4-[trans-4-(5-methoxypentyl)cyclohexyl]-benzene,
1-chloro-2-fluoro-4-[trans-4-(3-methoxypropyl)cyclohexyl]benzene,
1-chloro-2-fluoro-4-[trans-4-(3-ethoxypropyl)cyclohexyl]benzene,
1-chloro-2-fluoro-4-[trans-4-(3-propoxypropyl)cyclohexyl]benzene, 1-chloro-2-fluoro-4-[trans-4-(4-methoxybutyl)cyclohexyl]benzene,
1-chloro-2-fluoro-4-[trans-4-(4-ethoxybutyl)cyclo-hexyl]benzene,
1-chloro-2-fluoro-4-[trans-4-(5-methoxypentyl)cyclohexyl]benzene,
2-(p-chlorophenyl)-5-(3-methoxypropyl)pyridine,
2-(p-chlorophenyl)-5-(5-methoxypentyl)pyridine,
2-(p-chlorophenyl)-5-(3-methoxypropyl)pyrimidine,
2-(p-chlorophenyl)-5-(5-methoxypentyl)pyrimidine,
4-chloro-4'-(3-methoxypropyl)biphenyl,
4-chloro-4'-(5-methoxypentyl)biphenyl,
4-chloro-3-fluoro-4'-(3-methoxypropyl)biphenyl.

Example 2

A mixture of 4.6 g of trans-4-(4-chlorophenyl)-trans-4'-(3-methoxy-2-propenyl)[1,1'-bicyclohexyl] in 80 ml of ethyl acetate and 1 g of Raney nickel is hydrogenated in an autoclave for 10 hours at 60° C. and 5 kg/cm². The suspension is filtered and evaporated. The residue (4.5 g) is recrystallized twice from 30 ml of ethanol each time and gives 3.5 g of trans-4-(4-chloro-phenyl)-trans-4'-(3-methoxypropyl)[1,1'-bicyclohexyl]; m.p. (C—N) 73° C., cl.p. (N—I) 185.7° C.

The trans-4-(4-chlorophenyl)-trans-4'-(3-methoxy-2propenyl)[1,1'-bicyclohexyl] used as the starting material was prepared as follows:

a) A suspension, gassed with nitrogen, of 9.3 g of (methoxymethyl)triphenylphosphonium chloride in 40 ml of tetrahydro-furan is cooled to −5° C. and treated with 3.9 g of potassium tert.-butylate. The suspension is stirred at −5° C. for 10 minutes and at room temperature for 1 hour, again cooled to −5° C. and treated within 5 minutes with a solution of 12 g of trans-4'-(4-chloro-phenyl)-trans-4-[1,1'-bicyclohexyl]carboxaldehyde in 60 ml of tetrahydrofuran. After stirring at −5° C. for 10 minutes and at room temperature for 1 hour 100 ml of water are added thereto and the aqueous phase is extracted with 200 ml of ethyl acetate. The organic phase is washed with water, dried over sodium sulphate, filtered and evaporated. The residue is taken up with 100 ml of toluene and dissolved by heating to 70° C. and stirring for 30 minutes. The solution is cooled to room temperature, treated with 200 ml of hexane, stirred for 2 hours, filtered and washed with 70 ml of hexane/toluene (1:1 vol.). The filtrate is filtered over 200 g of silica gel and the column is rinsed with 500 ml of hexane/toluene (1:1 vol.). The filtrate is evaporated and gives 11 g of trans-4-(4-chlorophenyl)-trans-4'-(2-methoxy-vinyl)[1,1'-bicyclohexyl].

b) 5.5 g of trans-4-(4-chlorophenyl)-trans-4'-(2-methoxyvinyl)[1,1'-bicyclohexyl] in 60 ml of tetrahydrofuran and 20 ml of 9 percent hydrochloric acid are stirred at 60° C. for 3 hours. After cooling to room temperature the aqueous phase is extracted with 150 ml of ethyl acetate. The organic phase is washed with water, dried over sodium sulphate, filtered and evaporated. The residue gave 5 g of [trans-4'-(4-chlorophenyl)[1,1'-bicyclohexyl]-4-trans-yl]acetaldehyde.

c) A suspension, gassed with nitrogen, of 10.3 g of (methoxymethyl)triphenylphosphonium chloride in 50 ml of tetrahydro-furan is cooled to −5° C., treated with 4.5 g of potassium tert.-butylate, stirred at −5° C. for 10 minutes and at room temperature for 1 hour. After cooling the reaction mixture to −5° C. a solution of 5 g of [trans-4'-(4-chlorophenyl)[1,1'-bicyclohexyl]-4-trans-yl]acetaldehyde in 30 ml of tetrahydrofuran is added dropwise within 5 minutes, the mixture is stirred at −5° C. for 10 minutes and at room temperature for 1 hour, treated with 50 ml of water and the aqueous phase is extracted with 100 ml of ethyl acetate. The organic phase is washed with water, dried over sodium sulphate, filtered and concentrated. The residue is taken up in 70 ml of toluene and dissolved by heating to 70° C. and stirring for 30 minutes. The solution is cooled to room temperature, treated with 70 ml of hexane, stirred for 2 hours, filtered and washed with 40 ml of toluene/hexane (1:1 vol.). The filtrate is filtered over 100 g of silica gel and the silica gel is washed with 200 ml of hexane/toluene (1:1 vol.). The filtrate is concentrated and gives 4.6 g of trans-4-(4-chlorophenyl)-trans-4'-(3-methoxy-2-propenyl)]1,1'-bicyclohexyl].

The following compounds can be manufactured in an analogous manner:
trans-4-(4-chlorophenyl)-trans-4'-(3-ethoxypropyl)[1,1'-bicyclohexyl],
trans-4-(4-chlorophenyl)-trans-4'-(3-propoxypropyl)[1,1'-bicyclohexyl],
trans-4-(4-chlorophenyl)-trans-4'-(4-methoxybutyl)[1,1'-bicyclohexyl],
trans-4-(4-chlorophenyl)-trans-4'-(4-ethoxybutyl)[1,1'-bicyclohexyl],
trans-4-(4-chlorophenyl)-trans-4'-(5-methoxypentyl)[1,1'-bicyclohexyl],
trans-4-(3,4-dichlorophenyl)-trans-4'-(3-methoxypropyl)-[1,1'-bicyclohexyl],
trans-4-(3,4-dichlorophenyl)-trans-4'-(3-ethoxypropyl)-[1,1'-bicyclohexyl],
trans-4-(3,4-dichlorophenyl)-trans-4'-(3-propoxypropyl)-[1,1'-bicyclohexyl],
trans-4-(3,4-dichlorophenyl)-trans-4'-(4-methoxybutyl)-[1,1'-bicyclohexyl],
trans-4-(3,4-dichlorophenyl)-trans-4'-(4-ethoxybutyl)-[1,1'-bicyclohexyl],
trans-4-(3,4-dichlorophenyl)-trans-4'-(5-methoxypentyl)-[1,1'-bicyclohexyl],
trans-4-(4-chloro-3-fluorophenyl)-trans-4'-(3-methoxypropyl)[1,1'-bicyclohexyl],
trans-4-(4-chloro-3-fluorophenyl)-trans-4'-(3-ethoxypropyl)[1,1'-bicyclohexyl],
trans-4-(4-chloro-3-fluorophenyl)-trans-4'-(3-propoxypropyl)[1,1'-bicyclohexyl],
trans-4-(4-chloro-3-fluorophenyl)-trans-4'-(4-methoxybutyl)[1,1'-bicyclohexyl],
trans-4-(4-chloro-3-fluorophenyl)-trans-4'-(4-ethoxybutyl)[1,1'-bicyclohexyl],
trans-4-(4-chloro-3-fluorophenyl)-trans-4'-(5-methoxypentyl)[1,1'-bicyclohexyl],
2-(p-chlorophenyl)-5-[trans-4-(3-methoxypropyl)cyclohexyl]pyridine,
2-(p-chlorophenyl)-5-[trans-4-(3-methoxypropyl)cyclohexyl]pyrimidine,
trans-2-(p-chlorophenyl)-5-[trans-4-(3-methoxypropyl)cyclohexyl]-1,3-dioxane,
2-(p-chlorophenyl)-5-[4-(3-methoxypropyl)phenyl]pyridine,
2-(p-chlorophenyl)-5-[4-(3-methoxypropyl)phenyl]pyrimidine,
4-chloro-4'-[trans-4-(3-methoxypropyl)cyclohexyl]biphenyl, 4-chloro-4'-[trans-4-(3-ethoxypropyl)cyclohexyl]biphenyl,
4-chloro-4'-[trans-4-(4-methoxybutyl)cyclohexyl]biphenyl,
4-chloro-4'-[trans-4-(4-ethoxybutyl)cyclohexyl]biphenyl,
4-chloro-4'-[trans-4-(5-methoxypentyl)cyclohexyl]biphenyl,
4-chloro-3-fluoro-4'-[trans-4-(3-methoxypropyl)cyclohexyl]biphenyl
4-chloro-3-fluoro-4'-[trans-4-(3-ethoxypropyl)cyclohexyl]biphenyl
4-chloro-3-fluoro-4'-[trans-4-(4-methoxybutyl)cyclohexyl]biphenyl
4-chloro-3-fluoro-4'-[trans-4-(5-methoxypentyl)cyclohexyl]biphenyl
3,4-dichloro-4'-[trans-4-(3-methoxypropyl)cyclohexyl]biphenyl,
3,4-dichloro-4'-[trans-4-(4-methoxybutyl)cyclohexyl]biphenyl,
3,4-dichloro-4'-[trans-4-(5-methoxypentyl)cyclohexyl]biphenyl.

Example 3

5.5 g of trans-4-(4-chlorophenyl)-trans-4'-(2-methoxyvinyl)[1,1'-bicyclohexyl] are dissolved in 80 ml of ethyl acetate in an autoclave, treated with 1 g of Raney nickel and hydrogenated for 7 hours at 60° C. and 5 kg/cm². The suspension is filtered and evaporated and gives 5.4 g of crude trans-4-(4-chlorophenyl)-trans-4'-(2-methoxyethyl)[1,1'-bicyclohexyl]; m.p. (C—N) 61.2° C., cl.p. (N—I) 146° C.

The trans-4-(4-chlorophenyl)-trans-4'-(2-methoxyvinyl)-[1,1'-bicyclohexyl] used as the starting material is prepared in the following manner:

20.6 g of methoxymethyltriphenylphosphonium chloride and 12 g of [trans-4'-(4-chlorophenyl)[1,1'-bicyclohexyl]-trans-4-yl]carboxaldehyde are reacted as described in Example 2a) and give 11 g of trans-4-(4-chlorophenyl)-trans-4'-(2-methoxyvinyl)[1,1'-bicyclohexyl].

The following compounds can be manufactured in an analogous manner:

1-Chloro-4-[trans-4-(2-methoxyethyl)cyclohexyl]benzene,
1-chloro-4-[trans-4-(2-ethoxyethyl)cyclohexyl]benzene,
1-chloro-4-[trans-4-(2-propoxyethyl)cyclohexyl]benzene,
1-chloro-4-[trans-4-(2-butoxyethyl)cyclohexyl]benzene,
1,2-dichloro-4-[trans-4-(2-methoxyethyl)cyclohexyl]benzene,
1,2-dichloro-4-[trans-4-(2-ethoxyethyl)cyclohexyl]benzene,
1,2-dichloro-4-[trans-4-(2-propoxyethyl)cyclohexyl]benzene,
1-chloro-2-fluoro-4-[trans-4-(2-methoxyethyl)cyclohexyl]benzene,
1-chloro-2-fluoro-4-[trans-4-(2-ethoxyethyl)cyclo-hexyl]benzene,
1-chloro-2-fluoro-4-[trans-4-(2-propoxyethyl)cyclohexyl]benzene,
4-chloro-4'-(2-methoxyethyl)biphenyl,
4-chloro-4'-(2-ethoxyethyl)biphenyl,
4-chloro-3-fluoro-4'-(2-methoxyethyl)biphenyl,
2-(4-chlorophenyl)-5-(2-methoxyethyl)pyridine,
2-(4-chlorophenyl)-5-(2-ethoxyethyl)pyridine,
2-(4-chlorophenyl)-5-(2-methoxyethyl)pyrimidine,
2-(4-chlorophenyl)-5-(2-ethoxyethyl)pyrimidine,
trans-4-(4-chlorophenyl)-trans-4'-(2-methoxyethyl)[1,1'-bicyclohexyl],
trans-4-(4-chlorophenyl)-trans-4'-(2-ethoxyethyl)[1,1'-bicyclohexyl],
trans-4-(4-chlorophenyl)-trans-4'-(2-propoxyethyl)[1,1'-bicyclohexyl],
trans-4¹(3,4-dichlorophenyl)-trans-4'-(2-methoxyethyl)-[1,1'-bicyclohexyl],
trans-4¹(3,4-dichlorophenyl)-trans-4'-(2-ethoxyethyl)-[1,1'-bicyclohexyl],
trans-4-(4-chloro-3-fluorophenyl)-trans-4'-(2-methoxyethyl)[1,1'-bicyclohexyl],
trans-4-(4-chloro-3-fluorophenyl)-trans-4'-(2-ethoxyethyl)[1,1'-bicyclohexyl],
4-chloro-4'-[trans-4-(2-methoxyethyl)cyclohexyl]biphenyl,
4-chloro-4'-[trans-4-(2-ethoxyethyl)cyclohexyl]biphenyl,
3,4-dichloro-4'-[trans-4-(2-methoxyethyl)cyclohexyl]biphenyl,
4-chloro-3-fluoro-4-[trans-4-(2-methoxyethyl)cyclohexyl]biphenyl,
4-chloro-3-fluoro-4-[trans-4-(2-ethoxyethyl)cyclohexyl]biphenyl,
2-(4-chlorophenyl)-5-[trans-4-(2-methoxyethyl)cyclohexyl]pyridine,
2-(4-chlorophenyl)-5-[trans-4-(2-ethoxyethyl)cyclohexyl]pyridine,
2-(4-chlorophenyl)-5-[trans-4-(2-methoxyethyl)cyclohexyl]pyrimidine,
2-(4-chlorophenyl)-5-[trans-4-(2-ethoxyethyl)cyclohexyl]pyrimidine,
2-(4-chloro-3-fluorophenyl)-5-[trans-4-(2-methoxyethyl)cyclohexyl]pyridine,
2-(4-chloro-3-fluorophenyl)-5-[trans-4-(2-methoxyethyl)cyclohexyl]pyrimidine,
trans-2-(4-chlorophenyl)-5-[trans-4-(2-methoxyethyl)cyclohexyl]-1,3-dioxane.

Example 4

The properties of the compounds of formula I were investigated in binary mixtures of these compounds with 4-(trans-4-pentylcyclohexyl)benzonitrile. The threshold potential and the response times were measured at 22° C. in a TN cell (low bias tilt) having a plate separation of 8 μm; the 2.5-fold value of the threshold potential being chosen as the operating voltage. The corresponding data for pure 4-(trans-4-pentylcyclohexyl)benzo-nitrile are: cl.p. (N—I) 54.6° C., $V_{10}=1.62$ V, $t_{on}=30$ ms, $t_{off}=42$ ms, $\Delta n=0.120$.

BM-1

90 wt. % of 4-(trans-4-pentylcyclohexyl)benzonitrile
10 wt. % of trans-4-(4-chlorophenyl)-trans-4'-(2-methoxyethyl)[1,1'-bicyclohexyl].

Cl.p. (N—I) 60.1° C., $V_{10}=1.74$ V, $t_{on}=24$ ms, $t_{off}=41$ ms.

BM-2

80 wt. % of 4-(trans-4-pentylcyclohexyl)benzonitrile
20 wt. % of trans-4-(4-chlorophenyl)-trans-4'-(2-methoxyethyl)[1,1'-bicyclohexyl].

Cl.p. (N—I) 66.5° C., $V_{10}=1.74$ V, $t_{on}=25$ ms, $t_{off}=43$ ms.

BM-3

90 wt. % of 4-(trans-4-pentylcyclohexyl)benzonitrile 10 wt. % of trans-4-(4-chlorophenyl)-trans-4'-(3-methoxypropyl)[1,1'-bicyclohexyl].

Cl.p. (N—I) 64.0° C., $V_{10}=1.78$ V, $t_{on}=24$ ms, $t_{off}=39$ ms.

BM-4

80 wt. % of 4-(trans-4-pentylcyclohexyl)benzonitrile 20 wt. % of trans-4-(4-chlorophenyl)-trans-4'-(3-methoxypropyl)[1,1'-bicyclohexyl].

Cl.p. (N—I) 74.7° C., $V_{10}=1.88$ V, $t_{on}=24$ ms, $t_{off}=41$ ms.

BM-5

90 wt. % of 4-(trans-4-pentylcyclohexyl)benzonitrile 10 wt. % of 1-chloro-4-[trans-4-(5-methoxypentyl)cyclohexyl]benzene.

Cl.p. (N—I) 49.1° C., $V_{10}=1.52$ V, $t_{on}=25$ ms, $t_{off}=40$ ms.

BM-6

80 wt. % of 4-(trans-4-pentylcyclohexyl)benzonitrile 20 wt. % of 1-chloro-4-[trans-4-(5-methoxypentyl)cyclohexyl]benzene.

Cl.p. (N—I) 44.1° C., $V_{10}=1.53$ V, $t_{on}=23$ ms, $t_{off}=39$ ms.

What is claimed is:

1. A compound of the formula

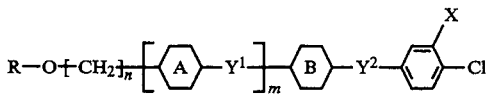

wherein R is alkyl of 1 to 12 carbon atoms; n is an integer from 2 to 7; ring A is trans-1,4-cyclohexylene or 1,4-phenylene; m is either 0 or 1; ring B is trans-1,4-cyclohexylene, 1,4-phenylene, pyridin-2,5-diyl, pyrimidin-2,5-diyl or pyrazine-2,5-diyl; or when m is 1, ring B also can be trans-1,3-dioxane-2,5-diyl; $Y^1$ and $Y^2$ each independently are a single covalent bond or —CH$_2$CH$_2$—; and X is hydrogen, fluorine or chlorine.

2. A compound according to claim 1, wherein R is a straight-chain alkyl group with 1 to 5 carbon atoms.

3. A compound according to claim 1, wherein ring A is trans-1,4-cyclohexylene.

4. A compound according to claim 1, wherein ring B is selected from the group consisting of trans-1,4-cyclohexylene and 1,4-phenylene.

5. A compound according to claim 1, wherein at least one of the groups $Y^1$ and $Y^2$ is a single covalent bond.

6. A compound according to claim 1, wherein m is 0, and ring B is trans-1,4-cyclohexylene.

7. A compound according to claim 1, wherein m is 0, and $Y^2$ is a single covalent bond.

8. A compound according to claim 1, wherein m is 1, rings A and B each are trans-1,4-cyclohexylene, and $Y^1$ and $Y^2$ each are a single covalent bond.

9. A compound according to claim 1, wherein m is 1, rings A and B each are trans-1,4-cyclohexylene, and $Y^1$ is —CH$_2$CH$_2$—.

10. A compound according to claim 1, wherein m is 1, ring A is trans-1,4-cyclohexylene, ring B is trans-1,3-dioxane-2,5-diyl, and $Y^1$ is a single covalent bond.

11. A compound according to claim 1, wherein m is 1, ring A is trans-1,4-cyclohexylene, $Y^1$ is —CH$_2$CH$_2$—, and ring B is trans-1,3-dioxane-2,5-diyl.

12. A compound according to claim 1, wherein m is 1, ring A is trans-1,4-cyclohexylene, $Y^1$ is a single covalent bond, ring B is 1,4-phenylene, and $Y^2$ is a single covalent bond.

13. A compound according to claim 1, wherein m is 1, ring A is trans-1,4-cyclohexylene, $Y^1$ is —CH$_2$CH$_2$—, ring B is 1,4-phenylene, and $Y^2$ is a single covalent bond.

14. A compound according to claim 1, wherein m is 1, ring A is trans-1,4-cyclohexylene, $Y^1$ is a single covalent bond, and ring B is 1,4-phenylene.

15. The compound of claim 1, 1-chloro-4-[trans-4-(5-methoxypentyl)cyclohexyl]benzene.

16. The compound of claim 1, trans-4-(4-chlorophenyl)-trans 4'-(3-methoxypropyl)[1,1'-bicyclohexyl].

17. The compound of claim 1, trans-4-(4-chlorophenyl)-trans 4'-(2-methoxyethyl)[1,1'-bicyclohexyl].

18. A compound of the formula

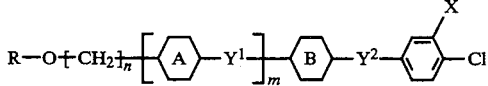

wherein R is alkyl of 1 to 12 carbon atoms; n is an integer from 2 to 7; m is 1; ring A is trans-1,4-cyclohexylene; ring B is trans-1,4-cyclohexylene or 1,4-phenylene; $Y_1$ and $Y_2$ are each single covalent bonds; and X is hydrogen, fluorine or chlorine.

* * * * *